United States Patent
Igarashi (12)

(10) Patent No.: US 7,037,598 B2
(45) Date of Patent: May 2, 2006

(54) LIGHT-EMITTING ELEMENT AND NOVEL IRIDIUM COMPLEXES

(75) Inventor: Tatsuya Igarashi, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 46 days.

(21) Appl. No.: 10/212,785

(22) Filed: Aug. 7, 2002

(65) Prior Publication Data

US 2003/0080342 A1     May 1, 2003

(30) Foreign Application Priority Data

Aug. 7, 2001   (JP)   ............ P.2001-239281

(51) Int. Cl.
   *H05B 33/14* (2006.01)
(52) U.S. Cl. ............ 428/690; 428/917; 313/504; 313/506; 257/102; 257/103
(58) Field of Classification Search ........ 428/690, 428/917; 313/504, 506; 257/102, 103; 546/2, 546/6
   See application file for complete search history.

(56) References Cited

U.S. PATENT DOCUMENTS

| | | | |
|---|---|---|---|
| 5,755,999 A * | 5/1998 | Shi et al. | 252/301.16 |
| 6,303,231 B1 | 10/2001 | Sawada et al. | 428/470 |
| 6,458,475 B1 * | 10/2002 | Adachi et al. | 428/690 |
| 6,660,410 B1 * | 12/2003 | Hosokawa | 428/690 |
| 6,893,743 B1 * | 5/2005 | Sato et al. | 428/690 |

| | | | |
|---|---|---|---|
| 2002/0028329 A1 * | 3/2002 | Ise et al. | 428/336 |
| 2002/0182441 A1 * | 12/2002 | Lamansky | 428/690 |

FOREIGN PATENT DOCUMENTS

| WO | WO 00/57676 A1 | 9/2000 |
|---|---|---|
| WO | WO 00/70655 A2 | 11/2000 |
| WO | WO 01/41512 A1 | 6/2001 |
| WO | WO 02/02714 A2 | 1/2002 |
| WO | WO 02/15645 A1 | 2/2002 |

OTHER PUBLICATIONS

Kwong et al., "Organic Light-emitting Devices Based on Phosphorescent Hosts and Dyes", Advanced Materials, vol. 12, No. 15, pp. 1134-1138 (Aug. 2000).*
U.S. Appl. No. 60/283,814.*
C.W. Tang et al, "Organic electroluminescent diodes", Appl. Phys. Lett., vol. 51, No. 12, (Sep. 21, 1987), pp. 913-915.
M.A. Baldo et al, "Very high-efficiency green organic light-emitting devices based on electrophosphorescence", Appl. Phys. Lett., vol. 75, No. 1, (Jul. 5, 1999), pp. 4-6.

* cited by examiner

*Primary Examiner*—Marie Yamnitzky
(74) *Attorney, Agent, or Firm*—Sughrue Mion, PLLC

(57) ABSTRACT

A light-emitting element comprising: a pair of electrodes; and at least one organic compound layer comprising a light-emitting layer provided between the electrodes, the light-emitting layer comprising at least one compound represented by formula (1) as defined herein, wherein the light-emitting layer comprises a host compound and the compound represented by the formula (1), and the host compound has an energy level of a lowest triplet excited state ($T_1$ level) of 62 kcal/mol (259 kJ/mol) to 85 kcal/mol (355 kJ/mol).

28 Claims, No Drawings

LIGHT-EMITTING ELEMENT AND NOVEL IRIDIUM COMPLEXES

FIELD OF THE INVENTION

The present invention relates to a light-emitting element capable of converting electric energy to light to emit light, which can be suitably used in the fields of display elements, displays, back lights, electrophotography, illumination sources, recording sources, exposing sources, reading sources, signs, signboards, interior decoration and optical communication, and to novel iridium complexes favorably used for the light-emitting element.

BACKGROUND OF THE INVENTION

In these days, research and development are being vigorously made on various display elements. Especially, organic electric field light-emitting (EL) elements have been noted as promising display elements since they emit light with a high luminance at a low voltage. For example, there have been known light-emitting elements prepared by forming an organic thin film through vacuum deposition of an organic compound (Applied Physics Letters, vol. 51, p. 913, 1987). The light-emitting elements described in this literature, wherein tris(8-hydroxyquinolinato) aluminum complex (Alq) is used as an electron transporting material and is formed into a layered structure together with a hole transporting material (an amine compound), show a markedly improved light-emitting performance in comparison with conventional single-layered elements.

In recent years, it has been vigorously investigated to apply the organic EL elements to a color display or a white light source. However, in order to develop a high-performance display and a white light source, it is necessary to improve properties of each of a blue light-emitting element, a green light-emitting element and a red light-emitting element.

As means for improving the properties of light-emitting elements, there have been reported green light-emitting elements utilizing emission of light from an orthometalated iridium complex (Ir (ppy)$_3$:Tris-Ortho-Metalated Complex of Iridium (III) with 2-phenylpyridine) (Applied Physics Letters, 75, 4 (1999)). This element shows an external quantum yield of 8%, which exceeds the conventionally believed upper limit as to an external quantum yield of 5%. However, since the color of emitted light is limited to green, it finds only limited applications to displays. Thus, it has been desired to develop elements capable of emitting other color than green with a high efficiency.

SUMMARY OF THE INVENTION

The present invention provides novel iridium complexes, blue light-emitting elements and multi-color light emitting elements containing a metal complex and showing a good light-emitting performance.

The above-described objects can be attained by the following items 1 to 20.

1. A light-emitting element comprising: a pair of electrodes; and at least one organic compound layer comprising a light-emitting layer provided between the electrodes, the light-emitting layer comprising at least one compound represented by the formula (1):

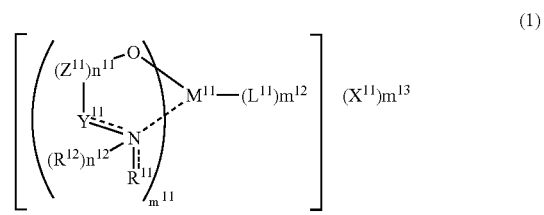

wherein $R^{11}$ represents a substituent, $R^{12}$ represents a hydrogen atom or a substituent, $Y^{11}$ represents a substituted or unsubstituted nitrogen atom or a substituted or unsubstituted carbon atom, $Z^{11}$ represents a linking group, $M^{11}$ represents a transition metal ion, $L^{11}$ represents a ligand, $X^{11}$ represents a counter ion, a bond between $Y^{11}$ and a nitrogen atom is a single bond or a double bond, a bond between $R^{11}$ and the nitrogen atom is a single bond or a double bond, $n^{11}$ represents 0 or 1, $n^{12}$ represents 0 or 1, providing that $n^{12}$ is 0, $Y^{11}$ and $R^{11}$ may be linked together to form a nitrogen-containing hetero ring, $m^{11}$ represents an integer of 1 to 3, $m^{12}$ represents an integer of 0 to 8, and $m^{13}$ represents an integer of 0 to 3, with at least one electron-withdrawing group being contained in the compound represented by the formula (1), wherein the light-emitting layer comprises a host compound and the compound represented by the formula (1), and the host compound has an energy level of a lowest triplet excited state ($T_1$ level) of 62 kcal/mol (259 kJ/mol) to 85 kcal/mol (355 kJ/mol).

2. The light-emitting element of item 1, wherein a layer adjacent to the light-emitting layer comprises a compound having an energy level of a lowest triplet excited state ($T_1$, level) of 62 kcal/mol (259 kJ/mol) to 85 kcal/mol (355 kJ/mol).

3. The light-emitting element of item 1 or 2, wherein the compound represented by the formula (1) is a compound represented by the formula (2):

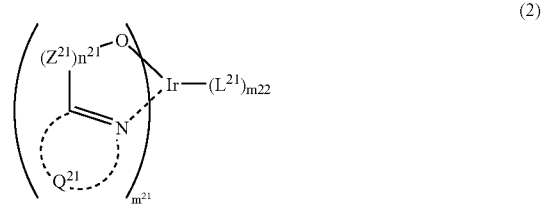

wherein $Z^{21}$ represents a linking group, $L^{21}$ represents a ligand, $n^{21}$ represents 0 or 1, $m^{21}$ represents an integer of 1 to 3, $m^{22}$ represents an integer of 0 to 4, and $Q^{21}$ represents atoms necessary for forming a nitrogen-containing hetero ring.

4. The light-emitting element of item 1 or 2, wherein the compound represented by the formula (1) is a compound represented by the formula (3):

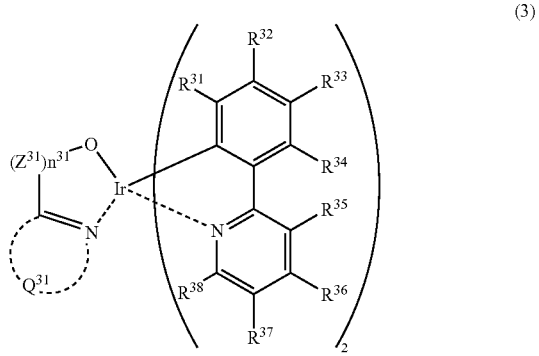

(3)

wherein $Z^{31}$ represents a linking group, $n^{31}$ represents 0 or 1, $Q^{31}$ represents atoms necessary for forming a nitrogen-containing hetero ring, and $R^{31}$, $R^{32}$, $R^{33}$, $R^{34}$, $R^{35}$, $R^{36}$, $R^{37}$ and $R^{38}$ each independently represents a hydrogen atom or a substituent.

5. The light-emitting element of any one of items 1 to 4, wherein the electron-withdrawing group has a Hammett's σ value of at least 0.1.

6. The light-emitting element of any one of items 1 to 5, wherein the electron-withdrawing group is one of a fluorine atom, a trifluoromethyl group, an acetyl group, a methanesulfonyl group, a trifluoroacetyl group, a trifluoromethanesulfonyl group and a cyano group.

7. The light-emitting element of item 1, 2, 5 or 6, wherein the compound represented by the formula (1) has at least one fluorine atom.

8. The light-emitting element of any one of items 1 to 7, which comprises a layer comprising a compound having an ionization potential of 5.9 eV or more between a cathode and the light-emitting layer.

9. A light-emitting element comprising: a pair of electrodes; and at least one organic compound layer comprising a light-emitting layer provided between the electrodes, the light-emitting layer comprising at least one compound represented by the formula (5):

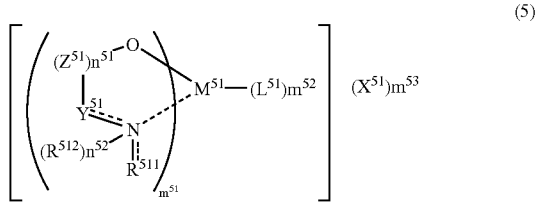

(5)

wherein $R^{511}$ represents a substituent, $R^{512}$ represents a hydrogen atom or a substituent, $Y^{51}$ represents a substituted or unsubstituted nitrogen atom or a substituted or unsubstituted carbon atom, $Z^{51}$ represents a linking group, $M^{51}$ represents a transition metal ion, $L^{51}$ represents a ligand forming non-carbon-metal bond, $X^{51}$ represents a counter ion, a bond between $Y^{51}$ and a nitrogen atom is a single bond or a double bond, a bond between $R^{511}$ and the nitrogen atom is a single bond or a double bond, $n^{51}$ represents 0 or 1, $n^{52}$ represents 0 or 1, providing that $n^{52}$ is 0, $Y^{51}$ and $R^{511}$ may be linked together to form a nitrogen-containing hetero ring, $m^{51}$ represents an integer of 1 to 3, $m^{52}$ represents an integer of 0 to 8, and $m^{53}$ represents an integer of 0 to 3.

10. The light-emitting element of item 9, wherein the compound represented by the formula (5) is a compound represented by the formula (6):

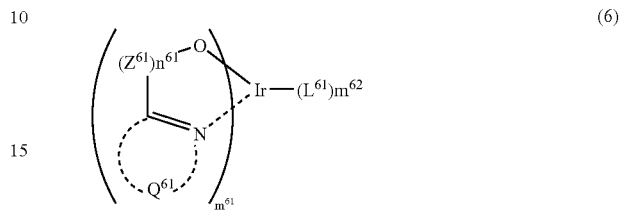

(6)

Wherein $Z^{61}$ represents a linking group, $L^{61}$ represents a ligand forming non-carbon-metal bond, $n^{61}$ represents 0 or 1, $m^{61}$ represents an integer of 1 to 3, $m^{62}$ represents an integer of 0 to 4, and $Q^{61}$ represents atoms necessary for forming a nitrogen-containing hetero ring.

11. The light-emitting element of item 10, wherein the compound represented by the formula (6) is a compound represented by the formula (7):

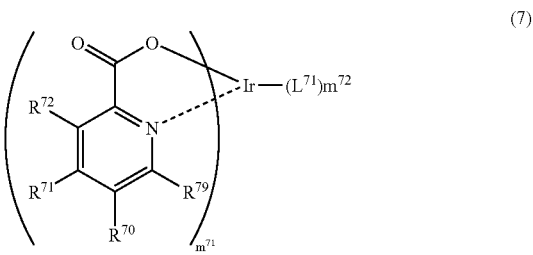

(7)

wherein $R^{70}$, $R^{71}$, $R^{72}$ and $R^{79}$ each independently represents a hydrogen atom or a substituent, $L^{71}$ represents a ligand forming non-carbon-metal bond, $m^{71}$ represents an integer of 1 to 3, and $m^{72}$ represents an integer of 0 to 4.

12. The light-emitting element of item 11, which comprises a layer comprising a compound having an ionization potential of 5.9 eV or more between a cathode and the light-emitting layer.

13. The light-emitting element of item 9, wherein $L^{51}$ represents a ligand which is attached to a metal atom with at least one atom selected from the group consisting of a nitrogen atom, an oxygen atom, a sulfur atom and a phosphorus atom.

14. The light-emitting element of item 9, wherein $L^{51}$ represents a bidentate ligand forming a non-carbon-metal bond.

15. The light-emitting element of item 9, wherein $L^{51}$ represents a bidentate ligand which is attached to a metal with two nitrogen atoms.

16. The light-emitting element of item 15, wherein the bidentate ligand is selected from bipyridyl, phenanthroline, pyrazolyl pyridine, benzimidazolyl pyridine and pyromethene.

17. The light-emitting element of item 9, wherein $L^{51}$ represents a bidentate ligand which is attached to a metal with a nitrogen atom and an oxygen atom.

18. The light-emitting element of item 17, wherein the bidentate ligand is picolinic acid or 2-hydroxymethylpyridine.

19. The light-emitting element of item 9, wherein $L^{51}$ represents a bidentate ligand which is attached to a metal with two oxygen atoms.

20. The light-emitting element of item 19, wherein the bidentate ligand is acetyl acetone or acetyl.

DETAILED DESCRIPTION OF THE INVENTION

The invention is described in more detail below.

Additionally, "-to-" as used herein means a range which includes the numbers before and after "to" as the maximum value and minimum value, respectively.

Descriptions on the formula (1) are given below. $R^{11}$ represents a substituent. Examples of the substituent include a group bound to $Y^{11}$ through a linking group to form a nitrogen-containing hetero ring (the nitrogen-containing hetero ring to be formed being exemplified by a pyridine ring, a pyrazine ring, a pyrimidine ring, a triazine ring, a pyrazole ring, an imidazole ring, a triazole ring, a pyrrolidine ring and a piperidine ring), an alkyl group (containing preferably 1 to 30, more preferably 1 to 20, particularly preferably 1 to 10 carbon atoms, and being exemplified by methyl, ethyl, iso-propyl, tert-butyl, n-octyl, n-decyl, n-hexadecyl, cyclopropyl, oyclopentyl and cyclohexyl), an alkenyl group (containing preferably 2 to 30, more preferably 2 to 20, particularly preferably 2 to 10 carbon atoms, and being exemplified by vinyl, allyl, 2-butenyl and 3-pentenyl), an alkynyl group (containing preferably 2 to 30, more preferably 2 to 20, particularly preferably 2 to 10 carbon atoms, and being exemplified by propargyl and 3-pentynyl), an aryl group (containing preferably 6 to 30, more preferably 6 to 20, particularly preferably 6 to 12, and being exemplified by phenyl, p-methylphenyl, naphthyl and anthranyl), an amino group (containing preferably 0 to 30, more preferably 0 to 20, particularly preferably 0 to 10 carbon atoms, and being exemplified by amino, methylamino, dimethylamino, diethylamino, dibenzylamino, diphenylamino and ditolylamino), an alkoxy group (containing preferably 1 to 30, more preferably 1 to 20, particularly preferably 1 to 10 carbon atoms, and being exemplified by methoxy, ethoxy, butoxy and 2-ethylhexyloxy), an aryloxy group (containing preferably 6 to 30, more preferably 6 to 20, particularly preferably 6 to 12 carbon atoms, and being exemplified by phenyloxy, 1-naphthyloxy and 2-naphthyloxy), a heterocyclic oxy group (containing preferably 1 to 30, more preferably 1 to 20, particularly preferably 1 to 12 carbon atoms, and being exemplified by pyridyloxy, pyrazinyloxy, pyrimidyloxy and quinolyloxy), an acyl group (containing preferably 1 to 30, more preferably 1 to 20, particularly preferably 1 to 12 carbon atoms, and being exemplified by acetyl, benzoyl, formyl and pivaloyl), an alkoxycarbonyl group (containing preferably 2 to 30, more preferably 2 to 20, particularly preferably 2 to 12 carbon atoms, and being exemplified by methoxycarbonyl and ethoxycarbonyl), an aryloxycarbonyl group (containing preferably 7 to 30, more preferably 7 to 20, particularly preferably 7 to 12 carbon atoms, and being exemplified by phenyloxycarbonyl), a sulfonyl group (containing preferably 1 to 30, more preferably 1 to 20, particularly preferably 1 to 12 carbon atoms, and being exemplified by mesyl and tosyl),a hydroxyl group, a heterocyclic group (containing preferably 1 to 30, more preferably 1 to 12 carbon atoms, with the hetero atom being exemplified by a nitrogen atom, an oxygen atom and a sulfur atom, and being specifically exemplified by imidazolyl, pyridyl, quinolyl, furyl, thienyl, piperidyl, morpholino, benzoxazolyl, benzimidazolyl, benzothiazolyl, carbazolyl and azepinyl), a sylyl group (containing preferably 3 to 40, more preferably 3 to 30, particularly preferably 3 to 24 carbon atoms, and being exemplified by trimethylsilyl and triphenylsilyl), a silyloxy group (containing preferably 3 to 40, more preferably 3 to 30, particularly preferably 3 to 24 carbon atoms, and being exemplified by trimethylsilyloxy and triphenylsilyloxy), and a group capable of forming a carbon-to-nitrogen double bond together with the adjacent nitrogen atom. These substituents may further be substituted by those substituents which are described hereinafter and are bound to the nitrogen atom in $Y^{11}$.

$R^{11}$ preferably represents a group bound to $Y^{11}$ through a linking group to form a nitrogen-containing hetero ring, an alkyl group, an aryl group, a hydroxyl group or an alkoxy group, more preferably represents a group bound to $Y^{11}$ through a linking group to form an aromatic nitrogen-containing hetero ring, and still more preferably represents a group bound to $Y^{11}$ through a linking group to form a pyridine ring.

The bond between $Y^{11}$ and the nitrogen atom represents a single bond or a double bond. The bond between $R^{11}$ and the nitrogen atom represents a single bond or a double bond. The bond between $Y^{11}$ and the nitrogen atom and the bond between $R^{11}$ and the nitrogen atom do not represent a double bond at the same time.

$R^{12}$ represents a hydrogen atom or a substituent. Examples of the substituent include those which have been illustrated with respect to $R^{11}$, and preferable examples thereof include an alkyl group, an aryl group and a heterocyclic group, with an alkyl group being more preferred.

$Y^{11}$ represents a substituted or unsubstituted nitrogen atom or a substituted or unsubstituted carbon atom, and may be bound to $R^{11}$ through a linking group to form a nitrogen-containing hetero ring (the nitrogen-containing hetero ring to be formed being exemplified by a pyridine ring, a pyrazine ring, a pyrimidine ring, a triazine ring, a pyrazole ring, an imidazole ring, a triazole ring, a pyrrolidine ring and a piperidine ring). As the substituent on the nitrogen atom in $Y^{11}$, there are illustrated those which have been illustrated with respect to $R^{11}$.

Examples of the substituent on the carbon atom in $Y^{11}$ include an alkyl group (containing preferably 1 to 30, more preferably 1 to 20, particularly preferably 1 to 10 carbon atoms, and being exemplified by methyl, ethyl, iso-propyl, tert-butyl, n-octyl, n-decyl, n-hexadecyl, cyclopropyl, cyclopentyl and cyclohexyl), an alkenyl group (containing preferably 2 to 30, more preferably 2 to 20, particularly preferably 2 to 10 carbon atoms, and being exemplified by vinyl, allyl, 2-butenyl and 3-pentenyl), an alkynyl group (containing preferably 2 to 30, more preferably 2 to 20,particularly preferably2 to 10 carbon atoms, and being exemplified by propargyl and 3-pentynyl), an aryl group (containing preferably 6 to 30, more preferably 6 to 20, particularly preferably 6 to 12, and being exemplified by phenyl, p-methylphenyl, naphthyl and anthranyl), an amino group (containing preferably 0 to 30, more preferably 0 to 20, particularly preferably 0 to 10 carbon atoms, and being exemplified by amino, methylamino, dimethylamino, diethylamino, dibenzylamino, diphenylamino and ditolylamino), an alkoxy group (containing preferably 1 to 30, more preferably 1 to 20, particularly preferably 1 to 10 carbon atoms, and being exemplified by methoxy, ethoxy, butoxy and 2-ethylhexyloxy), an aryloxy group (containing preferably 6 to 30, more preferably 6 to 20, particularly preferably 6 to 12 carbon atoms, and being exemplified by phenyloxy, 1-naphthyloxy and 2-naphthyloxy), a heterocyclic oxy group (containing preferably 1 to 30, more preferably 1 to 20, particularly preferably 1 to 12 carbon atoms, and being exemplified by pyridyloxy, pyrazinyloxy, pyrimidyloxy and quinolyloxy), an acyl group (containing preferably 1 to 30, more preferably 1 to 20, particularly preferably 1 to 12 carbon atoms, and being exemplified by acetyl, benzoyl, formyl and pivaloyl), an alkoxycarbonyl group (containing preferably 2 to 30, more preferably 2 to 20, particularly preferably 2 to 12 carbon atoms, and being exemplified by methoxycarbonyl and ethoxycarbonyl), an aryloxycarbonyl group (containing preferably 7 to 30, more preferably 7 to 20, particularly preferably 7 to 12 carbon atoms, and being exemplified by phenyloxycarbonyl), an acyloxy group (containing preferably 2 to 30, more preferably 2 to 20, particularly preferably 2 to 10 carbon atoms, and being exemplified by acetoxy and benzoyloxy), an acylamino group (containing preferably 2 to 30, more preferably 2 to 20, particularly preferably 2 to 10 carbon atoms, and being exemplified by acetylamino and benzoylamino), an alkoxycarbonylamino group (containing preferably 2 to 30, more preferably 2to 20,particularly preferably 2to 12carbon atoms, and being exemplified by methoxycarbonylamino), an aryloxycarbonylamino group (containing preferably 7 to 30, more preferably 7 to 20, particularly preferably 7 to 12 carbon atoms, and being exemplified by phenyloxycarbonylamino), a sulfonylamino group (containing preferably 1 to 30, more preferably 1 to 20, particularly preferably 1 to 12 carbon atoms, and being exemplified by methanesulfonylamino and benzenesulfonylamino), a sulfamoyl group (containing. preferably 0 to 30, more preferably 0 to 20, particularly preferably 0 to 12 carbon atoms, and being exemplified by sulfamoyl, methylsulfamoyl, dimethylsulfamoyl and phenylsulfamoyl), a carbamoyl group (containing preferably 1 to 30, more preferably 1 to 20, particularly preferably 1 to 12 carbon atoms, and being exemplified by carbamoyl, methylcarbamoyl, diethylcarbamoyl and phenylcarbamoyl), an alkylthio group (containing preferably 1 to 30, more preferably 1 to 20, particularly preferably 1 to 12 carbon atoms, and being exemplified by methylthio and ethylthio), an arylthio group (containing preferably 6 to 30, more preferably 6 to 20, particularly preferably 6 to 12 carbon atoms, and being exemplified by phenylthio), a heterocyclic thio group (containing preferably 1 to 30, more preferably 1 to 20, particularly preferably 1 to 12 carbon atoms, and being exemplified by pyridylthio, 2-benzimidazolylthio, 2-benzoxazolylthio and 2-benzothiazolylthio) , a sulfonyl group (containing preferably 1 to 30, more preferably 1 to 20, particularly preferably 1 to 12 carbon atoms, and being exemplified by mesyl and tosyl), a sulfinyl group (containing preferably 1 to 30, more preferably 1 to 20, particularly preferably 1 to 12 carbon atoms, and being exemplified by methanesulfinyl and benzenesulfinyl), a ureido group (containing preferably 1 to 30, more preferably 1 to 20, particularly preferably 1 to 12 carbon atoms, and being exemplified by ureido, methylureido and phenylureido), a phosphoric acid amide group (containing preferably 1 to 30, more preferably 1 to 20, particularly preferably 1 to 12 carbon atoms, and being exemplified by diethylphosphoric acid amide and phenylphosphoric acid amide), a hydroxyl group, a mercapto group, a halogen atom (e.g., a fluorine atom, a chlorine atom, a bromine atom or an iodine atom), a cyano group, a sulfo group, a carboxyl group, a nitro group, a hydroxamic acid group, a sulfino group, a hydrazino group, an imino group, a heterocyclic group (containing preferably 1 to 30, more preferably 1 to 12 carbon atoms, with the hetero atom being exemplified by a nitrogen atom, an oxygen atom and a sulfur atom, and being specifically exemplified by imidazolyl, pyridyl, quinolyl, furyl, thienyl, piperidyl, morpholino, benzoxazolyl, benzimidazolyl, benzothiazolyl, carbazolyl and azepinyl), a sylyl group (containing preferably 3 to 40, more preferably 3 to 30, particularly preferably 3 to 24 carbon atoms, and being exemplified by trimethylsilyl and triphenylsilyl) and a silyloxy group (containing preferably 3 to 40, more preferably 3 to 30, particularly preferably 3 to 24 carbon atoms, and being exemplified by trimethylsilyloxy and triphenylsilyloxy). These substituents may further be substituted by those substituents which are described hereinafter and are bound to the carbon atom in $Y^{11}$.

$Y^{11}$ preferably represents a group bound to $R^{11}$ through a linking group to form a nitrogen-containing hetero ring, more preferably represents a group bound to R11 through a linking group to form an aromatic nitrogen-containing hetero ring still more preferably represents a group bound to $R^{11}$ through a linking group to form a pyridine ring.

$Z^{11}$ represents a divalent linking group which links the oxygen atom in the formula (1) to $Y^{11}$. The linking group is not particularly limited, but examples thereof include a carbonyl linking group (>C=O), an alkylene group, an arylene group, a heteroarylene group, a nitrogen-containing heterocyclic linking group, an oxygen atom linking group (—O—), a nitrogen atom linking group (—NH—), a thiocarbonyl linking group (>C=S), a sulfoxide linking group (>S=O), a sulfonyl linking group (—SO$_2$—) and a linking group composed of the combination of these linking groups. $Z^{11}$ preferably represents a carbonyl linking group or an alkylene linking group.

$M^{11}$ represents a transition metal ion. The transition metal ion is not particularly limited, but is preferably iridium ion, platinum ion, rhenium ion or ruthenium ion, more preferably iridium ion or platinum ion, particularly preferably iridium ion.

$L^{11}$ represents a ligand. As the ligand, there are illustrated, for example, those ligands which are described in "Photochemistry and Photophysics of Coordination Compounds" written by H. Yersin and published by Springer-Verlag, 1987 and "Yuki Kinzoku Kagaku-Kiso To Oyo-" written by Akio Yamamoto and published by Shokabo K. K., 1982. Preferred examples thereof include a halogen ligand (e.g., a chlorine ligand or a fluorine ligand), a nitrogen-containing heterocyclic ligand (e.g., bipyridyl, phenanthroline, phenylpyridine, pyrazolylpyridine or benzimidazolylpyridine), a diketone ligand, a nitrile ligand, a CO ligand, an isonitrile ligand, a phosphorus ligand (e.g., a phosphine derivative, a phosphite derivative or a phosphinine derivative) and a carboxylic acid ligand (e.g., acetic acid ligand), and more preferred examples include bidentate nitrogen-containing heterocyclic ligands (e.g., bipydidyl, phenanthroline, phenylpyridine, pyrazolylpyridine and benzimidazolylpyridine).

$X^{11}$ represents a counter ion. The counter ion is not particularly limited, but is preferably an alkali metal ion, an alkaline earth metal ion, a halide ion, perchlorate ion, PF$_6$ ion, an ammonium ion (e.g., tetramethylammonium ion), borate ion or phosphonium ion, more preferably perchlorate ion or PF$_6$ ion. $n^{11}$ is 0 or 1, preferably 1.

$n^{12}$ represents 0 or 1. In the case where the bond between $Y^{11}$ and the nitrogen atom is a single bond and the bond between $R^{11}$ and the nitrogen atom is a single bond, $n^{12}$ represents 1. In the case where either the bond between $Y^{11}$ and the nitrogen atom or the bond between $R^{11}$ and the nitrogen atom is a double bond, $n^{12}$ represents 0.

$m^{11}$ represents an integer of 1 to 3, preferably 1 or 2. $m^{12}$ represents an integer of 0 to 8, preferably 0 to 3, more preferably 1 or 2. $m^{13}$ represents an integer of 0 to 3, preferably 0 or 1, more preferably 0. The combination of $m^{11}$, $m^{12}$ and $m^{13}$ is preferably such that the compound represented by the formula (1) becomes a neutral complex.

The compound represented by the formula (1) has at least one electron-withdrawing group within the compound. As the electron-withdrawing group, those are preferred which have a Hammett's σ value (σp value or σm value; reference: Chem. Rev. 1991, 91, 165.) of 0.1 or more, more preferably 0.3 or more.

As the above-described electron-withdrawing group, a fluorine atom, a trifluoromethyl group, an acetyl group, a methanesulfonyl group, a trifluoroacetyl group, a trifluoromethanesulfonyl group and a cyano group are preferred, a fluorine atom, a trifluoromethyl group, a trifluoroacetyl group and a trifluoromethane group are more preferred, a fluorine atom and a trifluoromethyl group are still more preferred, and a fluorine atom is particularly preferred.

The compound represented by the formula (1) preferably has at least one fluorine atom within the compound, more preferably has at least two fluorine atom within the compound. Such fluorine atom is contained preferably in the group represented by $Z^{11}$, $X^{11}$, $R^{11}$ or $L^{11}$, more preferably in $L^{11}$.

In the invention, the compounds represented by the formula (1) are preferably those compounds which are represented by the formula (2) and those compounds which are represented by the following formula (3) are more preferred.

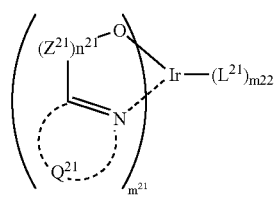

(2)

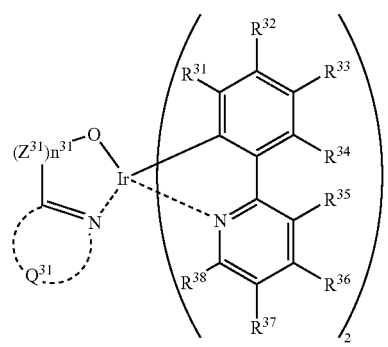

(3)

Descriptions are given below with respect to the formula (2). $Z^{21}$, $n^{21}$ and $L^{21}$ are respectively the same as $Z^{11}$, $n^{11}$ and $L^{11}$ described hereinbefore, and preferred examples thereof are also the same. $m^{21}$ represents an integer of 1 to 3, preferably 1 or 2. $m^{22}$ represents an integer of 0 to 4, preferably 1 or 2.

$Q^{21}$ represents atoms necessary for forming a nitrogen-containing hetero ring. The nitrogen-containing hetero ring formed by $Q^{21}$ is not particularly limited, but is preferably a pyridine ring, a pyrazine ring, a pyrimidine ring, a triazine ring, a thiazole ring, an oxazole ring, an imidazole ring, a pyrazole ring, a triazole ring, an oxadiazole ring or a condensed ring system containing such ring (e.g., a quinoline ring, a benzoxazole ring or a benzimidazole ring), more preferably a pyridine ring, a pyrazole ring, an imidazole ring or an oxazole ring, more preferably a pyridine ring, a pyrazole ring or an imidazole ring, still more preferably a pyridine ring.

The compound represented by the formula (2) has at least one fluorine atom within the compound, preferably has at least two fluorine atom within the compound. Such fluorine atom is contained preferably in the group represented by $Q^{21}$ or $L^{21}$, more preferably in $L^{21}$.

Descriptions are given below with respect to the formula (3). $Z^{31}$, $n^{31}$ and $Q^{31}$ are respectively the same as $Z^{21}$, $n^{21}$ and $Q^{21}$ described herein before, and preferred examples thereof are also the same. $R^{31}$, $R^{32}$, $R^{33}$, $R^{34}$ $R^{35}$, $R^{36}$, $R^{37}$ and $R^{38}$ each represent a hydrogen atom or a substituent. As the substituent, there are illustrated those which have been described as substituents on the carbon atom in $Y^{11}$ in the foregoing formula (1).

$R^{31}$ and $R^{33}$ each preferably represent a hydrogen atom, an alkyl group or a fluorine atom, more preferably represent a hydrogen atom or a fluorine atom. $R^{32}$ and $R^{34}$ each represent a hydrogen atom, an alkyl group or a fluorine atom, more preferably a fluorine atom.

$R^{35}$, $R^{36}$, $R^{37}$ and $R^{38}$ each preferably represent a hydrogen atom, an alkyl group, an alkoxy group or a substituted amino group. As the substituent in the substituted amino group, there are illustrated those which have been referred to as substituents on the carbon atom in $Y^{11}$ in the foregoing formula (1).

The compound represented by the formula (3). has at least one fluorine atom within the compound, preferably has at least two fluorine atom within the compound. Such fluorine atom is contained preferably in the group represented by $Q^{31}$, $R^{31}$, $R^{32}$, $R^{33}$, $R^{34}$, $R^{35}$, $R^{36}$, $R^{37}$ or $R^{38}$, more preferably in $R^{32}$ or $R^{34}$ and, still more preferably, $R^{32}$ or $R^{34}$ represents a fluorine atom. Particularly preferably, both $R^{32}$ and $R^{34}$ represent a fluorine atom.

Descriptions are given below with respect to the formula (5). $R^{511}$, $R^{512}$, $Y^{51}$, $Z^{51}$, $M^{51}$, $X^{51}$, $n^{51}$, $n^{52}$, $m^{51}$, $m^{52}$ and $m^{53}$ have the same meaning as $R^{11}$, $R^{12}$, $Y^{11}$, $Z^{11}$, $M^{11}$, $X^{11}$, $n^{11}$, $n^{12}$, $m^{11}$, $m^{12}$ and $m^{13}$, respectively, and preferred examples (ranges) thereof are also the same, respectively.

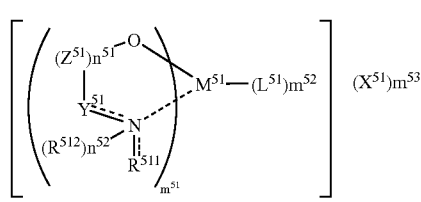

(5)

$L^{51}$ is preferably a ligand forming a non-carbon-metal bond (ligand which doesn't form a carbon-metal bond) , more preferably a bidentate ligand forming a non-carbon-metal bond. The ligand forming a non-carbon-metal bond is preferably a ligand attached to a metal atom with a nitrogen atom, oxygen atom, sulfur atom or phosphorus atom. More preferably, the ligand is a bidentate ligand attached to a metal atom with two different nitrogen atoms (e.g., bipyridyl, phenanthroline, pyrazolyl pyridine, benzimidazolyl pyridine, pyromethene), a bidentate ligand attached to a metal atom with a nitrogen atom and an oxygen atom (e.g., picolinic acid, 2-hydroxymethylpyridine) or a bidentate ligand attached to a metal atom with two different oxygen atoms (e.g., acetyl acetone, acetyl). Even more preferably, the ligand is a bidentate ligand attached to a metal atom with two different nitrogen atoms.

The compound represented by the formula (5) is preferably a compound represented by the formula (6), more preferably the formula (7).

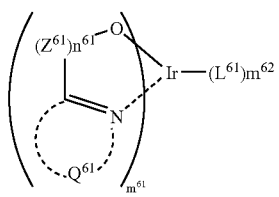
(6)

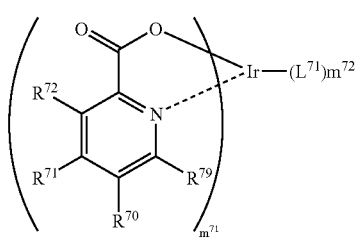
(7)

Descriptions are given below with respect to the formula (6). $Z^{61}$, $n^{61}$, $L^{61}$, $Q^{61}$ $m^{61}$ and $m^{62}$ have the same meaning as $Z^{51}$, $n^{51}$, $L^{51}$, $Q^{21}$, $m^{21}$ and $m^{22}$, respectively, and preferred examples thereof are also the same, respectively.

Descriptions are given below with respect to the formula (7). $R^{70}$, $R^{71}$, $R^{72}$, $R^{79}$, $L_{71}$, $m^{71}$ and $m^{72}$ have the same meaning as , $R^{50}$, $R^{51}$, $R^{52}$, $R^{49}$, $L^{51}$, $m^{61}$ and $m^{62}$, respectively, and preferred examples thereof are also the same, respectively.

The compounds of the invention may be low molecular compounds, oligomer compounds or polymer compounds (having a weight average molecular weight (in terms of polystyrene) of preferably 1000 to 5000000, more preferably 2000 to 1000000, still more preferably 3000 to 100000).

In the case where the compounds of the invention are polymer compounds, the structure represented by the formula (1) may be contained in the polymer main chain and/or polymer side chain. The polymer compounds of the invention may be homopolymer compounds or copolymer compounds. The compounds of the invention are preferably low molecular compounds.

Specific examples (illustrative compounds) of the invention are shown below which, however, do not limit the invention at all.

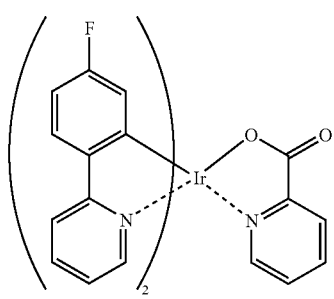
(1-1)

-continued

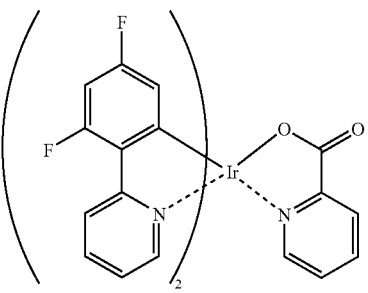
(1-2)

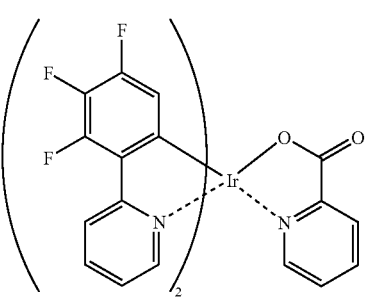
(1-3)

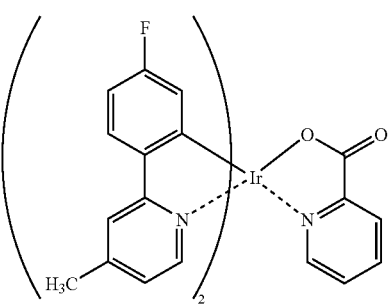
(1-4)

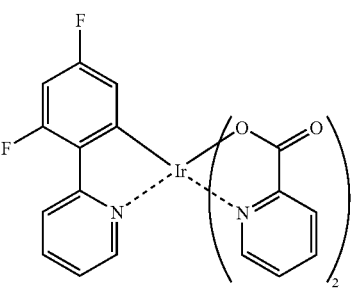
(1-5)

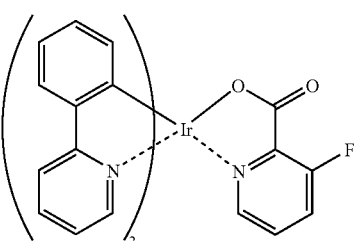
(1-6)

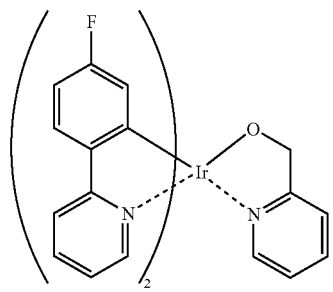
(1-7)
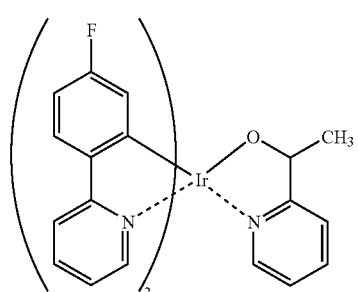
(1-8)
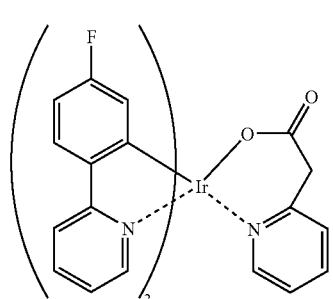
(1-9)
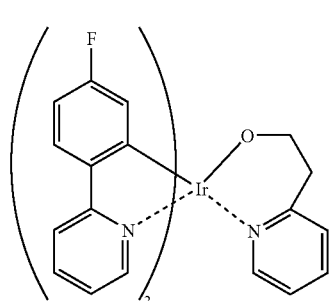
(1-10)
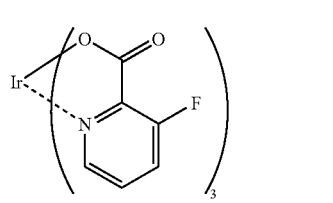
(1-11)
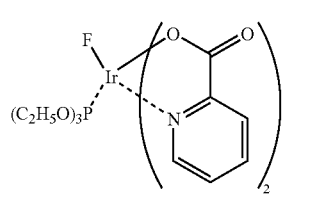
(1-12)
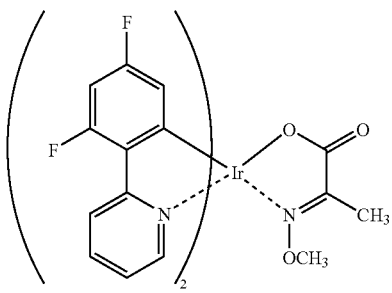
(1-13)
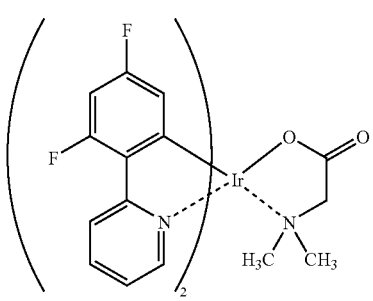
(1-14)
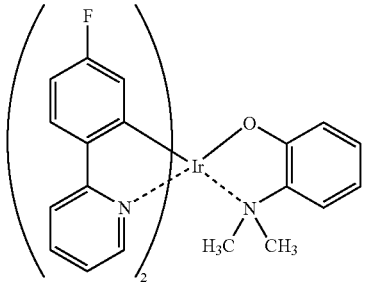
(1-15)
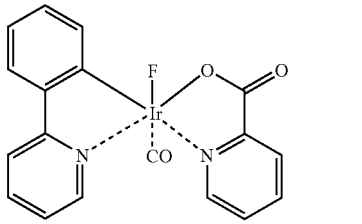
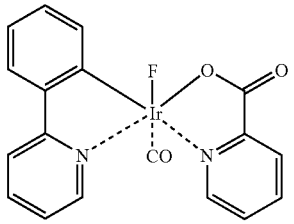
(1-16)
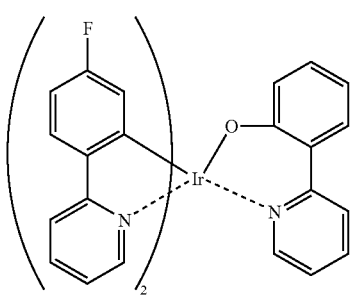
(1-17)

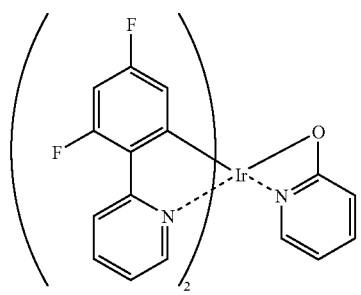
(1-18)
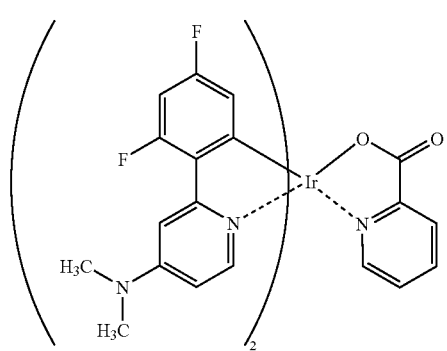
(1-19)
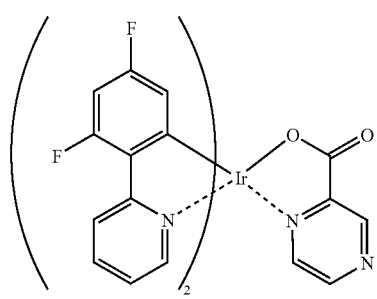
(1-20)
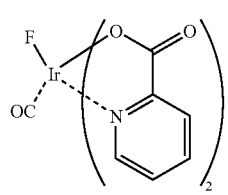
(1-21)
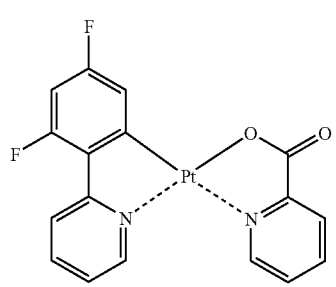
(1-22)
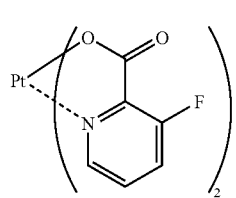
(1-23)
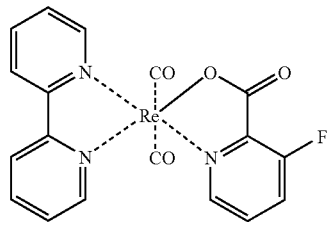
(1-24)
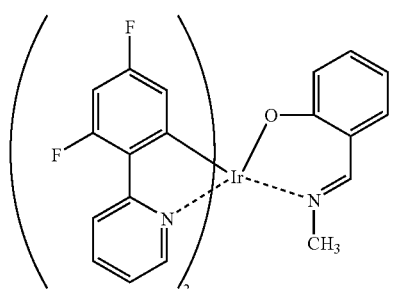
(1-25)
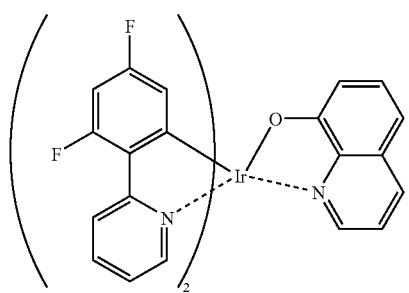
(1-26)
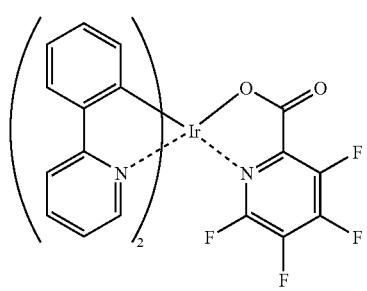
(1-27)
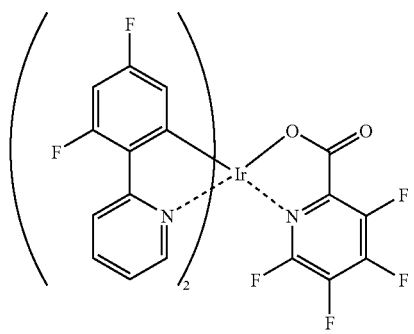
(1-28)

(1-29) 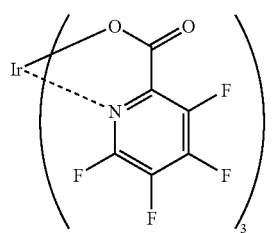
(1-30) 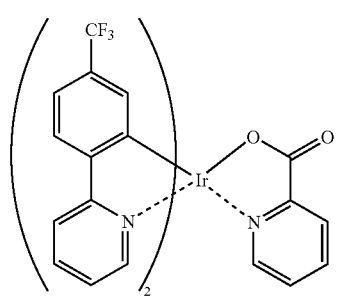
(1-31) 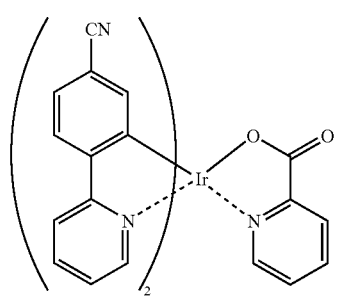
(1-32) 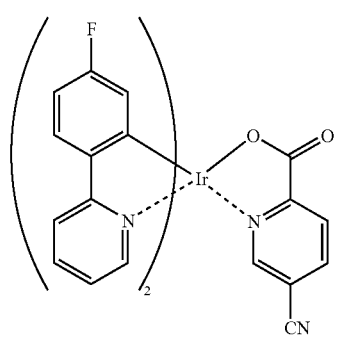
(1-33) 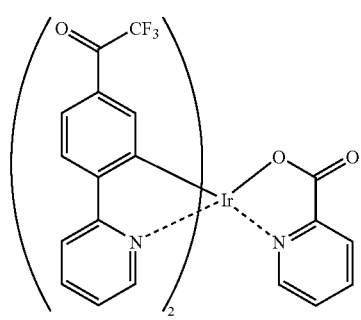
(1-34) 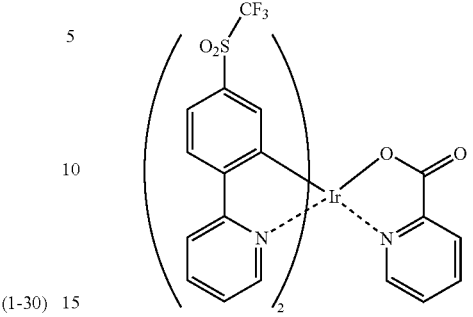
(1-35) 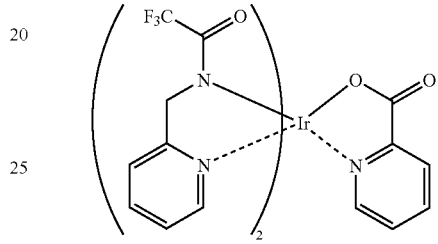
(1-36) 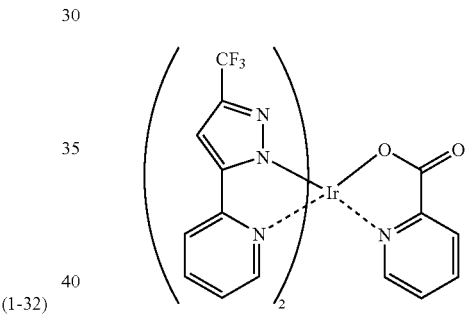
(1-37) 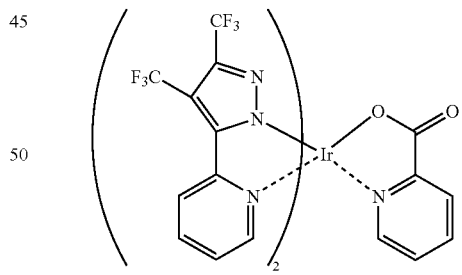
(1-38) 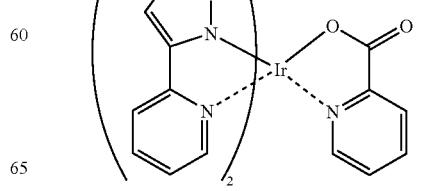

-continued (1-39) 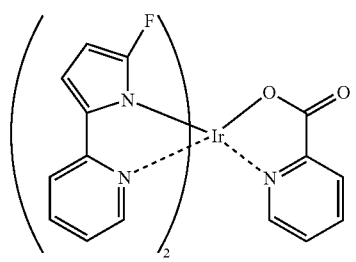

(1-40) 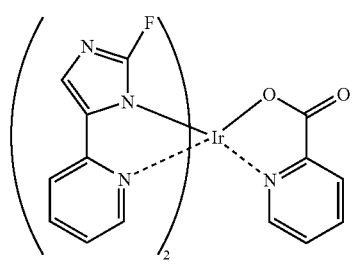

(1-41) 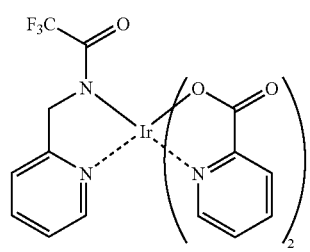

(1-42) 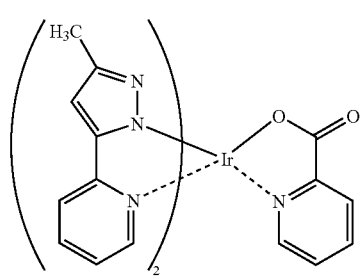

(1-43) 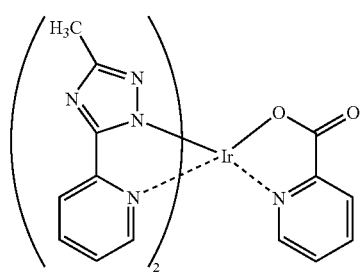

(1-44) 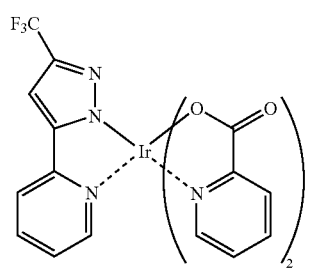

-continued (1-45) 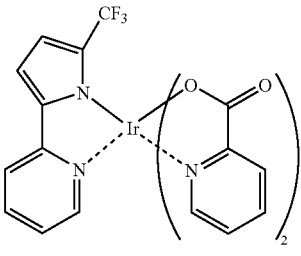

(1-46) 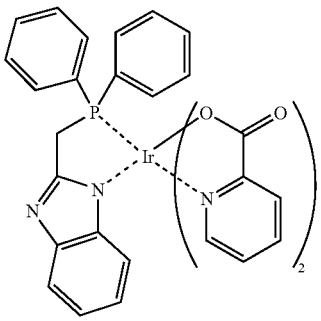

(1-47) 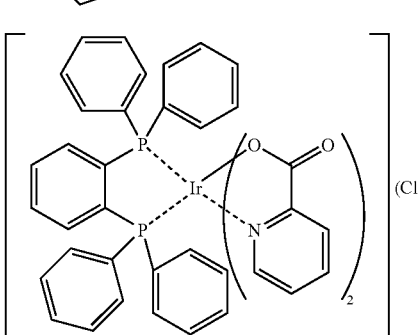

(1-48) 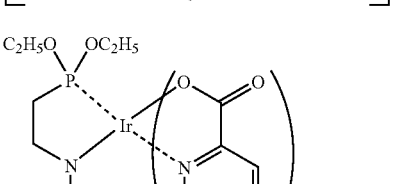

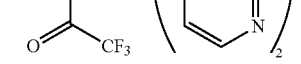

The compounds of the invention may be synthesized according to various known processes. For example, they may be synthesized by reacting a ligand or its dissociated body with a transition metal compound in the presence of a solvent (e.g., a halogen-containing solvent, an alcoholic solvent, an etheric solvent, a ketonic solvent or a nitrile solvent). They may also be synthesized by the reaction at a temperature lower than room temperature or heating (heating by microwave being effective as well as usual heating) in the absence of a solvent and in the presence or absence of abase (e.g., various inorganic or organic bases exemplified by sodium methoxide, potassium t-butoxide, triethylamine and potassium carbonate).

The compounds of the invention are also applicable to medical use, fluorescent brightening agents, materials for photography, UV ray absorbents, laser pigments, dyes for color filter and color-converting filter.

A light-emitting element containing the compound of the invention represented by the formulae (1) to (3) is described below. The light-emitting element of the invention is not particularly limited as to system, driving method and utilizing form as long as the aforesaid compound is contained. However, those light-emitting elements which contain the aforesaid compound as a light-emitting material are preferred. The term "light-emitting material" means a compound which is to be contained in a light-emitting layer or an organic compound layer including the light-emitting layer and emits light itself. Typical light-emitting elements include organic EL (electroluminescence) elements.

The light-emitting layer of the light-emitting element of the invention is constituted by a host compound and the compound represented by the formula (1), and the host compound has the minimum triplet excitation level ($T_1$ level) of preferably 62 kcal/mol(259 kJ/mol) to 85 kcal/mol (355 kJ/mol), more preferably, is constituted by a host compound and the compound represented by the formula (1), and the host compound has the minimum triplet excitation level ($T_1$ level) of 65 kcal/mol (272 kJ/mol) to 80 kcal/mol (334 kJ/mol).

As the host compound for the light-emitting element of the invention satisfying the above-described physical property requirement, those host compounds are preferred which are described in Japanese Patent Application Nos. 197135/2001 and 76704/2001, with the host compounds described in Japanese Patent Application No. 197315/2001 being more preferred. Preferred range of the host compounds described in Japanese Patent Application No. 197135/2001 is as described in the specification.

In the light-emitting element of the invention, T1 level of a compound contained in the layer adjacent to to the light-emitting layer is preferably 62 kcal/mol (259 kJ/mol) to 85 kcal/mol (855 kJ/mol), more preferably 65 kcal/mol (272 kJ/mol) to 80 kcal/mol (334 kJ/mol)

As the compound to be contained in the layer adjacent to the light-emitting layer, which satisfies the above-described physical property requirement, those hole transporting materials and electron transporting materials are preferred which are described in Japanese Patent Application No. 197135/2001. Preferred ranges of the hole transporting materials and electron transporting materials described in Japanese Patent Application No. 197135/2001 are as described in the specification.

The light-emitting element of the invention is an element wherein a light-emitting layer or a plurality of organic compound layers (organic layers) including a light-emitting layer are formed between a pair of electrodes of anode and cathode and may have a hole injecting layer, a hole transporting layer, an electron injecting layer, an electron transporting layer and a protective layer in addition to the light-emitting layer, with these layers optionally also performing functions of other layers. Various materials may be used for forming respective layers.

The light-emitting element of the invention containing the compound represented by the formula (1) to (3) contains the compound in the light-emitting layer or the organic compound layers including the light-emitting layer in an amount of preferably 0.1% by weight to 100% by weight, more preferably 1% by weight to 50% by weight, particularly preferably 1% by weight to 20% by weight.

In the light-emitting element of the invention, it is preferred to use a layer containing a compound having an ionization potential of 5.9 eV or more (more preferably 6.0 eV or more) between the cathode and the light-emitting layer, and it is more preferred to use an electron transporting layer of 5.9 eV or more in ionization potential.

Method for forming the organic layer of the light-emitting element containing the compound of the invention is not particularly limited, and there may be employed a resistance heating deposition method, an electron beam method, a sputtering method, a molecular layer-accumulating method, a coating method, an ink jet method, a printing method and a transfer method, with the resistance heating deposition method, the coating method and the transfer method being preferred in view of performance and production.

The anode functions to feed holes to the hole injecting layer, the hole transporting layer and the light-emitting layer, and a metal, an alloy, a metal oxide, an electroconductive compound or a mixture thereof may be used for the anode, with a material having a work function of 4 eV or more being preferred.

Specific examples thereof include conductive metal oxides such as tin oxide, zinc oxide, indium oxide and indium tin oxide (ITO) ,metals such as gold, silver, chromium and nickel, mixtures or layered products of the metal and the conductive metal oxide, inorganic conductive substances such as copper iodide and copper sulfide, organic conductive materials such as polyaniline, polythiophene and polypyrrole, and layered products of these and ITO, with conductive metal oxides being preferred. In particular, in view of productivity, high conductivity and transparency, ITO is preferred.

Thickness of the anode may properly be selected depending upon the kind of the material, but is preferably 10 nm to 5 um, more preferably 50 nm to 1 um, still more preferably 100 nm to 500 nm.

As the anode, those which are formed as a layer on, for example, soda-lime glass, alkali-free glass or a transparent resin substrate are used. In the case of using glass, alkali-free glass is preferably used in order to reduce the amount of ion released from the glass. Also, in the case of using soda-lime glass, it is preferred to provide a barrier coat of silica on the glass.

Thickness of the substrate is not particularly limited as long as a sufficient mechanical strength is obtained. In the case of using glass, glass of commonly 0.2 mm or more, preferably 0.7 mm or more, in thickness is used.

Various methods may be employed for forming the anode depending upon kind of the material used. In the case of, for example, ITO, the anode film is formed by the electron beam method, the sputtering method, the resistance heating deposition method, a chemical reaction method (e.g., a sol-gel method) or a method of coating a dispersion of indium tin oxide.

The anode may be subjected to a treatment of, for example, washing to reduce the voltage for driving the element and enhance light-emitting efficiency. In the case of, for example, ITO, UV-ozone treatment or plasma treatment is effective.

The cathode functions to feed electrons to the electron injecting layer, the electron transporting layer and the light-emitting layer, and is selected taking into consideration adhesion to the layer adjacent to the cathode such as the electron injecting layer, the electron transporting layer or the light-emitting layer, ionization potential and stability. As materials for the cathode, there are illustrated a metal, an alloy, a metal halide, a metal oxide, an electroconductive compound or a mixture thereof may be used.

Specific examples of the cathode include an alkali metal (e.g., Li, Na or K) and the fluoride or oxide thereof, an alkaline earth metal (e.g., Mg or Ca) and the fluoride or oxide thereof, gold, silver, lead, aluminum, sodium-potassium alloy or a mixed metal thereof, lithium-aluminum alloy or a mixed metal thereof, magnesium-silver alloy or a mixed metal thereof, and a rare earth metal such as indium or ytterbium, with a material having a work function of 4 eV or less being preferred. More preferably, aluminum, lithium-aluminum alloy or a mixed metal thereof, and magnesium-silver alloy or a mixed metal thereof.

The cathode may be of a single-layered structure of the above-described compound or the mixture or of a layered structure containing the above-described compound or the mixture. For example, a layered structure of aluminum/lithium fluoride or aluminum/lithium oxide is preferred.

Thickness of the cathode may properly be selected depending upon the kind of the material, but is preferably 10 nm to 5 μm, more preferably 50 nm to 1 μm, still more preferably 100 nm to 1 μm.

For forming the cathode, there may be employed a method such as the electron beam method, the sputtering method, the resistance heating deposition method or a coating method. It is possible to deposit a single metal or to deposit two or more components at the same time. Further, a plurality of metals may simultaneously be deposited to form an alloy electrode, or a previously prepared alloy may be deposited.

As to sheet resistance of the anode and the cathode, the lower, the better. A resistance of several hundreds $\Omega/\square$ or less is preferred.

As the material for the light-emitting layer, any of those may be used which can form a layer that, when an electric field is applied thereto, permits injection of holes from the anode, the hole injecting layer or the hole transporting layer and injection of electrons from the cathode, the electron injecting layer or the electron transporting layer, functions to migrate injected charges, and provides a site for recombination of the hole and the electron. In addition to the compounds of the invention, there are illustrated benzoxazole, benzimidazole, benzothiazole, styrylbenzene, polyphenyl, diphenylbutadiene, tetraphenylbutadiene, naphthalimide, coumarin, perylene, perynone, oxadiazole, aldazine, pyralidine, cyclopentadiene, bis-styrylanthracene, quinacridone, pyrrolopyridine, thiadiazolopyridine, cyclopentadiene, styrylamine, aromatic dimethylidene compound or various metal complexes represented by metal complexes or rare earth complexes of 8-quinolinol, polymer compounds such as polythiophene or polyphenylene, organic silane, iridium-tris-phenylpyridine complex, transition metal complexes represented by platinum-porphyrin complex, and the derivatives thereof.

Thickness of the light-emitting layer is not particularly limited, but is preferably 1 nm to 5 μm, more preferably 5 nm to 1 μm, still more preferably 10 nm to 500 nm.

Method for forming the light-emitting layer is not particularly limited, and there may be employed a resistance heating deposition method, an electron beam method, a sputtering method, a molecular layer-accumulating method, a coating method (spin coating method or dip coating method), an ink jet method, a printing method, an LB method and a transfer method, with the resistance heating deposition method and the coating method being preferred.

The light-emitting layer may be formed by a single compound or a plurality of compounds. Also, number of the light-emitting layer may be one or more. A plurality of the light-emitting layers may emit lights of different colors to thereby emit a white light. A white light may be emitted from a single layer. In the case where a plurality of the light-emitting layers are formed, each light-emitting layer may be formed by a single material or a plurality of compounds.

As the materials for the hole injecting layer and the hole transporting layer, those materials may be used which have one of the function of injecting holes from the anode side, the function of transporting holes, and the function of blocking electrons injected from the cathode.

Specific examples thereof include carbazole, triazole, oxazole, oxadiazole, imidazole, polyarylalkane, pyrazoline, pyrazolone, phenylenediamine, arylamine, amino-substituted chalcone, styrylanthracene, fluorenone, hydrazone, stilbene, silazane, aromatic tertiary amine compound, stilylamine compound, aromatic dimethylidene compound, porphyrin compound, polysilane compound, conductive high molecular oligomer such as poly(N-vinylcarbazole), aniline copolymer, thiophene oligomer and polythiophene, organic silane, carbon film, the compounds of the invention and the derivatives thereof.

Thickness of the hole injecting layer and the hole transporting layer is not particularly limited, but is preferably 1 nm to 5 μm, more preferably 5 nm to 1 μm, still more preferably 10 nm to 500 nm. The hole injecting layer and the hole transporting layer may be of a single layer structure composed of one or more of the above-described materials, or may be of a multi-layer structure composed of a plurality of layers having the same composition or different compositions.

Method for forming the hole injecting layer or the hole transporting layer is not particularly limited, and there may be employed a vacuum deposition method, an LB method, a coating method of dissolving or dispersing the aforesaid hole injecting and transporting material in a solvent (e.g., spin coating method, cast coating method or dip coating method), an ink jet method, a printing method and a transfer method. In the coating method, the material may be dissolved or dispersed together with the resin component.

As the resin component, there are illustrated, for example, polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin and silicone resin.

As the materials for the electron injecting layer and the electron transporting layer, those materials may be used which have one of the function of injecting electrons from the cathode side, the function of transporting electrons, and the function of blocking holes injected from the anode.

Specific examples thereof include triazole, oxazole, oxadiazole, imidazole, fluorenone, anthraquinodimethane, anthrone, diphenylquinone, thiopyran dioxide, carbodiimide, fluorenylidenemethane, distyrylpyrazine, tetracarboxylic acid anhydrides of aromatic compounds such as naphthalene and perylene, phthalocyanine, metal complex of 8-quinolinol, metal phthalocyanine, and various metal complexes represented by metal complexes containing benzoxazole or benzothiazole as ligand, organic silane, and the derivatives thereof.

Thickness of the electron injecting layer and the electron transporting layer is not particularly limited, but is preferably 1 nm to 5 um, more preferably 5 nm to 1 um, still more preferably 10 nm to 500 nm. The electron injecting layer and the electron transporting layer may be of a single layer structure composed of one or more of the above-described materials, or may be of a multi-layer structure composed of a plurality of layers having the same composition or different compositions.

As a method for forming the electron injecting layer and the electron transporting layer, there may be employed a vacuum deposition method, an LB method, a coating method of dissolving or dispersing the aforesaid electron injecting and transporting material in a solvent (e.g., spin coating method, cast coating method or dip coating method), an ink jet method, a printing method and a transfer method. In the coating method, the material may be dissolved or dispersed together with the resin component and, as the resin component, there may be used, for example, those which have been illustrated with respect to the hole injecting and transporting layer;

As materials for the protective layer, any material may be used that can prevent invasion of substances capable of deteriorating the light-emitting element, such as moisture or oxygen, into the element.

Specific examples thereof include metals such as In, Sn, Pb, Au, Cu, Ag, Al, Ti and Ni, metal oxides such as Mgo, SiO, $SiO_2$, $Al_2O_3$, GeO, NiO, CaO, BaO, $Fe_2O_3$, $Y_2O_3$ and $TiO_2$, metal fluorides such as $MgF_2$, LiF, $AlF_3$ and $CaF_2$, nitrides such as $SiN_x$ and $SiO_xN_y$, polyethylene, polypropylene, polymethyl methacrylate, polyimide, polyurea, polytetrafluoroethylene, polychlorotrifluoroethylene, polydichlorodifluoroethylene, copolymer between chlorotrifluoroethylene and dichlorodifluoroethylene, a copolymer obtained by copolymerizing tetrafluoroethylene with a monomer mixture containing at least one comonomer, a fluorine-containing copolymer having a cyclic structure in the main chain of the copolymer, a water-absorbing substance showing a water absorption of 1% or more, and a moisture barrier material showing a water absorption of 0.1% or less.

Method for forming the protective layer is not particularly limited, either, and there may be employed a vacuum deposition method, a sputtering method, a reactive sputtering method, an MBE (Molecular Beam Epitaxy) method, a cluster ion beam method, an ion plating method, a plasma polymerization method (high frequency-excited ion plating method), a plasma CVD method, a laser CVD method, a heat CVD method, a gas source CVD method, a coating method, a printing method and a transfer method. In the coating method, the material may be dissolved or dispersed together with the resin component.

The light-emitting element of the invention can be suitably used in the fields of display elements, displays, back lights, electrophotography, illumination sources, recording sources, exposing sources, reading sources, signs, signboards, interior decoration and optical communication.

EXAMPLES

Examples of the invention are described below which, however, do not limit the invention in any way.

Synthesis of Compound 1

200 ml of diethylene glycol dimethyl ether and 100 ml of water were added to 3.45 g of 2,4-difluorophenyl borate and 25 g of 2-bromopyridine, and 33.5 g of sodium carbonate, palladium carbon (Pd content: 10% by weight) and 0.1 g of triphenylphosphine were added thereto, followed by stirring the mixture for 5 hours under reflux. The resultant solution was cooled to room temperature, and 500 ml of ethyl acetate and 300 ml of water were added thereto, followed by filtering the mixture through sellaite (made by Wako Junyaku K. K.). The organic layer was washed twice with 100 ml of water, and dried over sodium sulfate, followed by concentrating the organic layer. The resultant concentrate was purified through column chromatography (by developing with chloroform, then with chloroform/methanol (=5/1 by volume) to obtain 15 g of pale yellow liquid. To 3.75 g of the resultant pale yellow liquid were added 50 ml of 2-methoxyethanol, 30 ml of water and 5.0 g of $K_3IrCl_6$, followed by stirring for 4 hours under reflux. After cooling to room temperature, the precipitated solid was filtered out to obtain 4 g of the pale yellow solid of compound 1.

Synthesis of the Illustrative Compound 1-2

10 ml of chloroform was added to 0.2 g of the compound 1 and 1.88 g of sodium picolinate, and the resultant mixture was stirred for 3 hours under reflux. The reaction solution was cooled to room temperature, purified through column chromatography (by developing with dichloromethane, then with dichloromethane/methanol (=10/1 by volume) to obtain 0.15 g of the pale yellow solid of illustrative compound 1-2. Structure of the compound 1-2 was confirmed by measuring mass spectrum. The compound 1-2 emitted a blue phosphorescence.

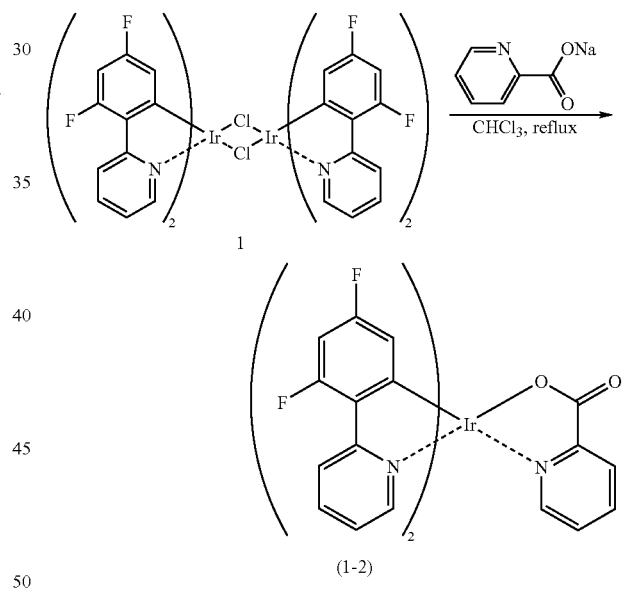

Evaluation of Light-emitting Properties as a Light-emitting Element

Comparative Example 1

A washed ITO substrate was placed in a depositing apparatus, and TPD (N,N'-diphenyl-N,N'-di(m-tolyl)benzidine) was deposited thereon in a thickness of 50 nm, then compound A and compound B were codeposited thereon with a ratio (by weight) of 1:17 in a thickness of 36 nm, followed by depositing azole compound C thereon in a thickness of 36 nm. A patterned mask (mask providing a light-emitting area of 4 mm×5 mm) was provided on the organic thin layers and, after depositing lithium fluoride in a thickness of 3 nm within the depositing apparatus, aluminum was deposited in a thickness of 60 nm to prepare a light-emitting element. A current constant voltage was applied to the resultant EL element using a Source Measure Unit 2400 made by Toyo Tekunika K. K., and luminance was measured using a luminance meter, BM-8, made by Topkon K. K. and wavelength of emitted light was measured using a Spectrum analyzer, PMA-11, made by Hamamatsu Photonics K. K. As a result, there was obtained a green light emission with Elmax (maximum wavelength of emitted light) of 518 nm and a chromaticity value of (0.31, 0.61). The external quantum efficiency of the element (calculated from luminance of emitted light, spectrum of emitted light, current density and relative luminosity curve) was 7.2%.

Comparative Example 2

A light-emitting element was prepared and evaluated in the same manner as in Comparative Example 1 except for using compound D in place of compound A. As a result, there was obtained a green light emission.

Compound A

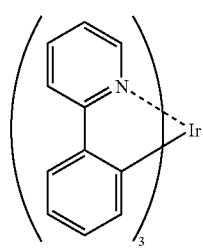

Compound B

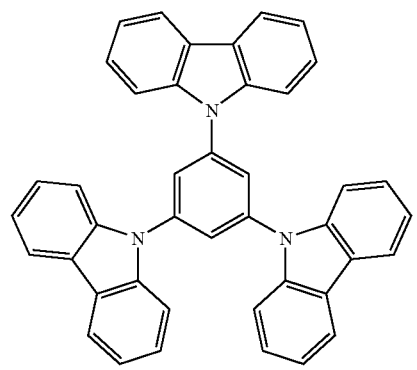

Compound C

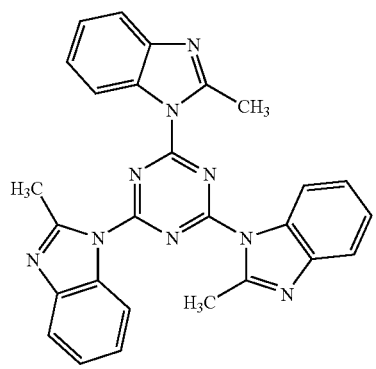

Compound D

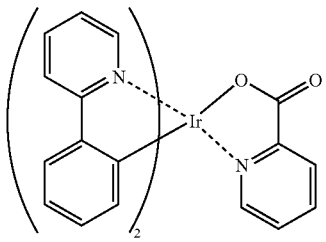

Example 1

A light-emitting element was prepared and evaluated in the same manner as in Comparative Example 1 except for using the compound 1-2 of the invention in place of compound A. As a result, there was obtained a blue light emission with Elmax of 472 nm and a chromaticity value of (0.18, 0.38). The external quantum efficiency of the element (calculated from luminance of emitted light, spectrum of emitted light, current density and relative luminosity curve) was 9.4%.

Blue light-emitting elements can also be prepared by using other compounds of the invention. Also, it is possible to prepare a white light-emitting element by using a red light-emitting material in combination.

The light-emitting element of the invention can emit a blue light with a small chromaticity value, and is excellent in external quantum efficiency.

What is claimed is:

1. A light-emitting element comprising:
    a pair of electrodes; and
    at least one organic compound layer comprising a light-emitting layer provided between the electrodes,
    the light-emitting layer comprising at least one compound represented by the formula (1):

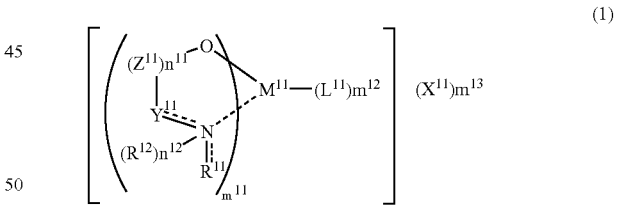

wherein $R^{11}$ represents a substituent, $R^{12}$ represents a hydrogen atom or a substituent, $Y^{11}$ represents a substituted or unsubstituted nitrogen atom or a substituted or unsubstituted carbon atom, $Z^{11}$ represents a linking group, $M^{11}$ represents a transition metal ion, $L^{11}$ represents a ligand, $X^{11}$ represents a counter ion, a bond between $Y^{11}$ and a nitrogen atom is a single bond or a double bond, a bond between $R^{11}$ and the nitrogen atom is a single bond or a double bond, $n^{11}$ represents 0 or 1, $n^{12}$ represents 0 or 1, provided that when $n^{12}$ is 0, $Y^{11}$ and $R^{11}$ may be linked together to form a nitrogen-containing hetero ring, $m^{11}$ represents an integer of 1 to 3, $m^{12}$ represents an integer of 0 to 8, and $m^{13}$ represents an integer of 0 to 3, with at least one electron-withdrawing group being contained in the compound represented by the formula (1), wherein the light-emitting layer comprises a host compound and the compound represented by the formula (1), and the host compound has an energy level of a lowest triplet excited state ($T_1$ level) of 62 kcal/mol (259 kJ/mol) to 85 kcal/mol (355 kJ/mol) and, wherein a layer adjacent to the light-emitting layer comprises a compound having an energy level of a lowest triplet excited state ($T_1$ level) of 62 kcal/mol (259 kJ/mol) to 85 kcat/mol (355 kJ/mol).

2. The light-emitting element of claim 1, wherein the compound represented by the formula (1) is a compound represented by the formula (2):

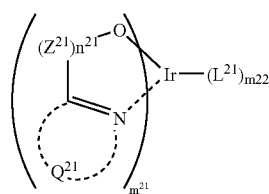

(2)

wherein $Z^{21}$ represents a linking group, $L^{21}$ represents a ligand, $n^{21}$ represents 0 or 1, $in^{21}$ represents an integer of 1 to 3, $in^{22}$ represents an integer of 0 to 4, and $Q^{21}$ represents atoms necessary for forming a nitrogen-containing hetero ring.

3. The light-emitting element of claim 1, wherein the compound represented by the formula (1) is a compound represented by the formula (3):

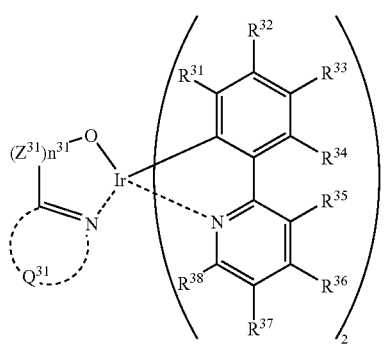

(3)

wherein $Z^{31}$ represents a linking group, $n^{31}$ represents 0 or 1, $Q^{31}$ represents atoms necessary for forming a nitrogen-containing hetero ring, and $R^{31}$, $R^{32}$, $R^{33}$, $R^{34}$, $R^{35}$, $R^{36}$, $R^{37}$ and $R^{38}$ each independently represents a hydrogen atom or a substituent.

4. The light-emitting element of claim 1, wherein the electron-withdrawing group has a Hammett's σ value of at least 0.1.

5. The light-emitting element of claim 1, wherein the electron-withdrawing group is one of a fluorine atom, a trifluoromethyl group, an acetyl group, a methanesulfonyl group, a trifluoroacetyl group, a trifluoromethanesulfonyl group and a cyano group.

6. The light-emitting element of claim 1, wherein the compound represented by the formula (1) has at least one fluorine atom.

7. The light-emitting element of claim 1, which comprises a layer comprising a compound having an ionization potential of 5.9 eV or more between a cathode and the light-emitting layer.

8. The light-emitting element of claim 1, wherein the light-emitting layer comprises a host compound and the compound represented by the formula (1), and the host compound has an energy level of a lowest triplet excited state (Ti level) of 65 kcal/mol (272 kJ/mol) to 80 kcal/inol (334 kJ/mol).

9. The light-emitting element of claim 1, wherein $M^{11}$ represents rhenium ion or ruthenium ion.

10. The light-emitting element of claim 1, wherein $M^{11}$ is iridium ion, $m^{11}$ is 2 and $m^{12}$ is 1.

11. The light-emitting element of claim 1, wherein $Z^{11}$ represents an alkylene group, an arylene group, a heteroarylene group, a nitrogen-containing heterocyclic linking group, an oxygen atom linking group, a nitrogen atom linking group, a thiocarbonyl linking group, a sulfoxide linking group, a sulfonyl linking group and a linking group composed of a combination of these linking groups.

12. The light-emitting element of claim 1, wherein $Y^{11}$ represents a substituted or unsubstituted nitrogen atom and $Y^{11}$ and $R^{11}$ may be linked together to form a nitrogen-containing hetero ring when $n^{12}$ is 0.

13. A light-emitting element comprising:
a pair of electrodes; and
at least one organic compound layer comprising a light-emitting layer provided between the electrodes,
the light-emitting layer comprising at least one compound represented by the formula (5):

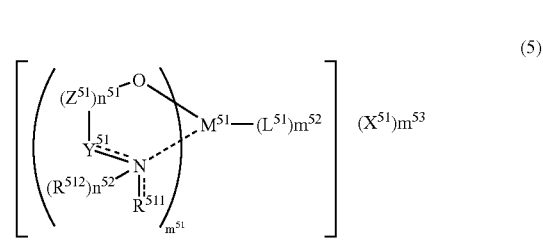

(5)

wherein $R^{511}$ represents a substituent, $R^{512}$ represents a hydrogen atom or a substituent, $Y^{51}$ represents a substituted or unsubstituted nitrogen atom or a substituted or unsubstituted carbon atom, $Z^{51}$ represents an alkylene group, a heteroarylene group, a nitrogen-containing heterocyclic linking group, an oxygen atom linking group, a nitrogen atom linking group, a thiocarbonyl linking group, a sulfoxide linking group, a sulfonyl linking group and a linking group composed of a combination of these linking groups, $M^{51}$ represents a transition metal ion, $L^{51}$ represents a ligand that forms at least one bond with a metal and at least one of these bonds is a non-carbon-metal bond, $X^{51}$ represents a counter ion, a bond between $Y^{51}$ and a nitrogen atom is a single bond or a double bond, a bond between $R^{511}$ and the nitrogen atom is a single bond or a double bond, $n^{51}$ represents, $n^{52}$ represents 0 or 1, provided that when $n^{52}$ is 0, $Y^{51}$ and $R^{511}$ may be linked together to form a nitrogen-containing hetero ring, $m^{51}$ represents an integer of 1 to 3, $m^{52}$ represents an integer of 0 to 8, and $m^{53}$ represents an integer of 0 to 3.

14. The light-emitting element of claim 13, wherein the compound represented by the formula (5) is a compound represented by the formula (6):

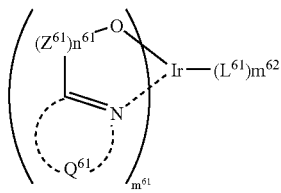

wherein $Z^{61}$ has the same meaning as $Z^{51}$, $L^{61}$ represents a ligand that forms at least one bond with a metal and at least one of these bonds is a non-carbon-metal bond, $n^{61}$ represents 1, $m^{61}$ represents an integer of 1 to 3, $m^{62}$ represents an integer of 0 to 4, and $Q^{61}$ represents atoms necessary for forming a nitrogen-containing hetero ring.

15. The light-emitting element of claim 13, wherein $L^{51}$ represents a ligand which is attached to a metal atom with at least one atom selected from the group consisting of a nitrogen atom, an oxygen atom, a sulfur atom and a phosphorus atom.

16. The light-emitting element of claim 13, wherein $L^{51}$ represents a bidentate ligand forming a non-carbon-metal bond.

17. The light-emitting element of claim 13, wherein $L^5$ represents a bidentate ligand which is attached to a metal with two nitrogen atoms.

18. The light-emitting element of claim 7, wherein the bidentate ligand is selected from bipyridyl, phenanthroline, pyrazolyl pyridine, benzimidazolyl pyridine and pyromethene.

19. The light-emitting element of claim 13, wherein $L^{51}$ represents a bidentate ligand which is attached to a metal with a nitrogen atom and an oxygen atom.

20. The light-emitting element of claim 19, wherein the bidentate ligand is picolinic acid or 2-hydroxymethylpyridine.

21. The light-emitting element of claim 13, wherein $L^{51}$ represents a bidentate ligand which is attached to a metal with two oxygen atoms.

22. The light-emitting element of claim 21, wherein the bidentate ligand is acetyl acetone or acetyl.

23. A light-emitting element comprising:
a pair of electrodes; and
at least one organic compound layer comprising a light-emitting layer provided between the electrodes,
the light-emitting layer comprising at least one compound represented by the formula (5):

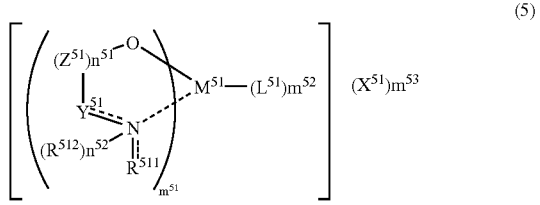

wherein $R^{511}$ represents a substituent, $R^{512}$ represents a hydrogen atom or a substituent, $Y^{51}$ represents a substituted or unsubstituted nitrogen atom or a substituted or unsubstituted carbon atom, $Z^{51}$ represents a linking group, $M^{51}$ represents a transition metal ion, $L^{51}$ represents a bidentate ligand which is attached to a metal with two nitrogen atoms, $X^{51}$ represents a counter ion, a bond between $Y^{51}$ and a nitrogen atom is a single bond or a double bond, a bond between $R^{511}$ and the nitrogen atom is a single bond or a double bond, $n^{51}$ represents 0 or 1, $n^{52}$ represents 0 or 1, provided that when $n^{52}$ is 0, $Y^{51}$ and $R^{511}$ may be linked together to form a nitrogen-containing hetero ring, $m^{51}$ represents an integer of 1 to 3, $m^{52}$ represents an integer of 1 to 8, and $m^{53}$ represents an integer of 0 to 3.

24. A light-emitting element according to claim 23, wherein the bidentate ligand is selected from bipyridyl, phenanthroline, pyrazolyl pyridine, benzimidazolyl pyridine and pyromethene.

25. A light-emitting element comprising:
a pair of electrodes; and
at least one organic compound layer comprising a light-emitting layer provided between the electrodes,
the light-emitting layer comprising at least one compound represented by the formula (5):

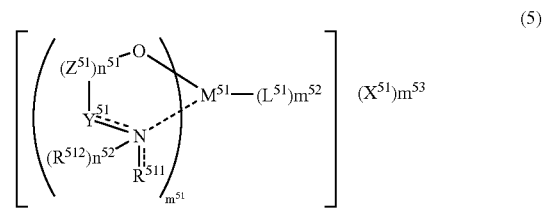

wherein $R^{511}$ represents a substituent, $R^{512}$ represents a hydrogen atom or a substituent, $Y^{51}$ represents a substituted or unsubstituted nitrogen atom or a substituted or unsubstituted carbon atom, $Z^{51}$ represents a linking group, $M^{51}$ represents a transition metal ion, $L^{51}$ represents a bidentate ligand which is attached to a metal with a nitrogen atom and an oxygen atom wherein the bidentate ligand is picolinic acid or 2-hydroxymethylpyridine, $X^{51}$ represents a counter ion, a bond between $Y^{51}$ and a nitrogen atom is a single bond or a double bond, a bond between $R^{511}$ and the nitrogen atom is a single bond or a double bond, $n^{51}$ represents 0 or 1, $n^{52}$ represents 0 or 1, provided that when $n^{52}$ is 0, $Y^{511}$ and $R^{511}$ may be linked together to form a nitrogen-containing hetero ring, $m^{51}$ represents an integer of 1 to 3, $m^{52}$ represents an integer of 1 to 8, and $in^{53}$ represents an integer of 0 to 3.

26. A light-emitting element comprising:
a pair of electrodes; and
at least one organic compound layer comprising a light-emitting layer provided between the electrodes,
the light-emitting layer comprising at least one compound represented by the formula (5):

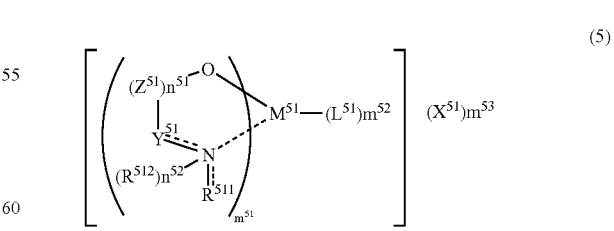

wherein $R^{511}$ represents a substituent, $R^{512}$ represents a hydrogen atom or a substituent, $Y^{51}$ represents a substituted or unsubstituted nitrogen atom or a substituted or unsubstituted carbon atom, $Z^{51}$ represents a linking group, $M^{51}$ represents a transition metal ion, $L^{51}$ represents a bidentate ligand which is attached to a metal with two oxygen atoms, $X^{51}$ represents a counter ion, a bond between $Y^{51}$ and a nitrogen atom is a single bond or a double bond, a bond between $R^{511}$ and the nitrogen atom is a single bond or a double bond, $n^{51}$ represents 0 or 1, $n^{52}$ represents 0 or 1, provided that when $n^{52}$ is 0, $Y^{51}$ and $R^{511}$ may be linked together to form a nitrogen-containing hetero ring, $m^{51}$ represents an integer of 1 to 3, $in^{52}$ represents an integer of 1 to 8, and $m^{53}$ represents an integer of 0 to 3.

27. A light-emitting element according to claim 26, wherein the bidentate ligand is acetyl acetone or acetyl.

28. A light-emitting element comprising:
    a pair of electrodes; and
    at least one organic compound layer comprising a light-emitting layer provided between the electrodes,
    the light-emitting layer comprising at least one compound represented by formula (7):

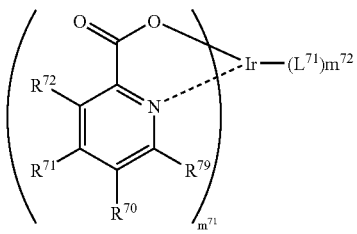

(7)

wherein $R^{70}$, $R^{71}$, $R^{72}$ and $R^{79}$ each independently represents a hydrogen atom or a substituent, $L^{71}$ represents a ligand forming a non-carbon-metal bond and each bond between the ligand $L^{71}$ and the metal Ir is a non-carbon metal bond, $m^{71}$ represents an integer of 1 to 3, and $m^{72}$ represents an integer of 0 to 4.

* * * * *